United States Patent
Edwards et al.

(10) Patent No.: US 6,470,219 B1
(45) Date of Patent: Oct. 22, 2002

(54) APPARATUS AND METHOD FOR TREATING FEMALE URINARY INCONTINENCE

(75) Inventors: Stuart D. Edwards, Portola Valley; Peter Edelstein, Woodside; Hong Li, San Diego, all of CA (US)

(73) Assignee: Novasys Medical, Inc., Newark, CA (US)

( * ) Notice: Subject to any disclaimer, the term of this patent is extended or adjusted under 35 U.S.C. 154(b) by 0 days.

(21) Appl. No.: 09/678,500

(22) Filed: Oct. 2, 2000

(51) Int. Cl.[7] .............................................. A61B 18/18
(52) U.S. Cl. ....................... 607/101; 607/104; 607/138; 606/41
(58) Field of Search ..................... 604/103.03, 103.07, 604/103.11, 103.14, 113, 114; 606/27–31, 32, 34, 41, 108, 129, 191–192; 607/115–116, 122, 126, 124, 133, 1–3, 40–41, 96–101, 104–105, 138; 600/372–375, 380

(56) References Cited

U.S. PATENT DOCUMENTS

| | | | |
|---|---|---|---|
| 5,366,490 A | * 11/1994 | Edwards et al. ............. | 128/898 |
| 5,454,782 A | 10/1995 | Perkins ......................... | 604/20 |
| 5,458,596 A | 10/1995 | Lax et al. | |
| 5,569,241 A | 10/1996 | Edwards ....................... | 606/41 |
| 5,588,960 A | 12/1996 | Edwards et al. | |
| 5,957,920 A | 9/1999 | Baker .......................... | 606/33 |
| 5,964,755 A | 10/1999 | Edwards ....................... | 606/41 |
| 6,077,257 A | * 6/2000 | Edwards et al. ........ | 604/101.03 |
| 6,091,995 A | 7/2000 | Ingle et al. | |
| 6,254,598 B1 | * 7/2001 | Edwards et al. .............. | 606/41 |

* cited by examiner

Primary Examiner—Kennedy Schaetzle
Assistant Examiner—Kristen Droesch
(74) Attorney, Agent, or Firm—Fish & Neave; Nicola A. Pisano

(57) ABSTRACT

Apparatus for remodeling in the urinary tract of a human female comprising a remodeling device having a shaft with a profile and with proximal and distal extremities. A handle is secured to the proximal extremity of the shaft. A member is mounted on the distal extremity of the shaft. A plurality of needle electrodes are carried by the distal extremity of the shaft and are disposed circumferentially of the shaft. A pusher is carried by the handle for moving the needle electrodes from a retracted position in which they are within the profile of the shaft and an extended position in which they extend sidewise beyond the profile of the shaft. A pump is connected to the handle for supplying a cooling liquid to the distal extremity of the shaft so that it exits from the shaft in the vicinity of the needle electrodes. An RF generator is coupled to the handle and to the needle electrodes for supplying radio frequency energy to the needle electrodes.

25 Claims, 5 Drawing Sheets

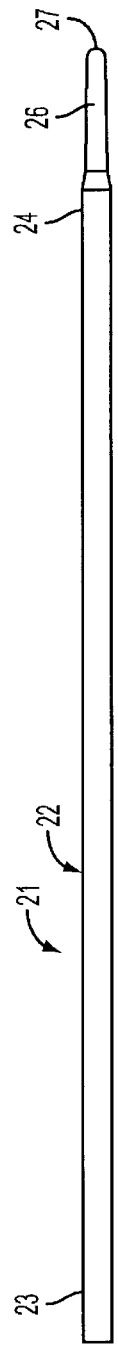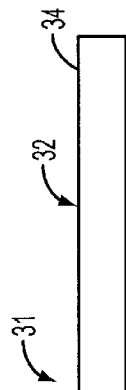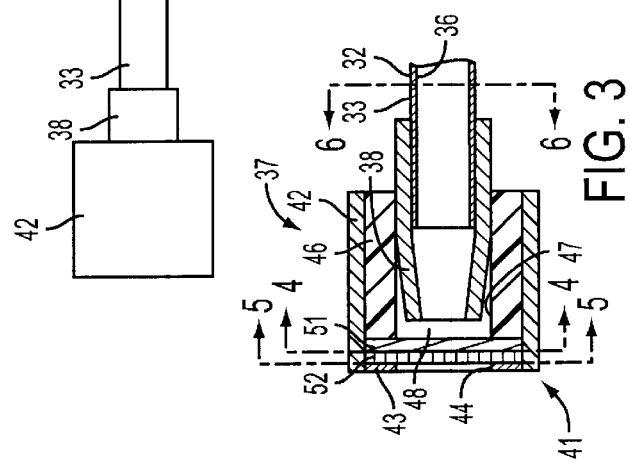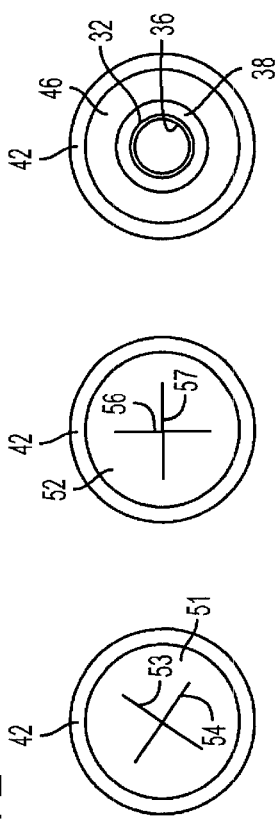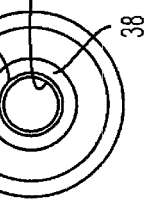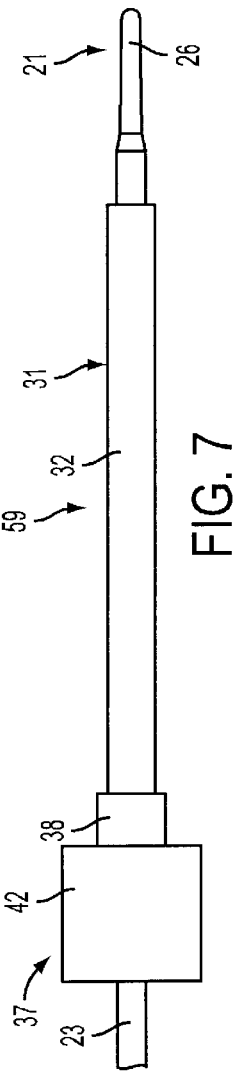

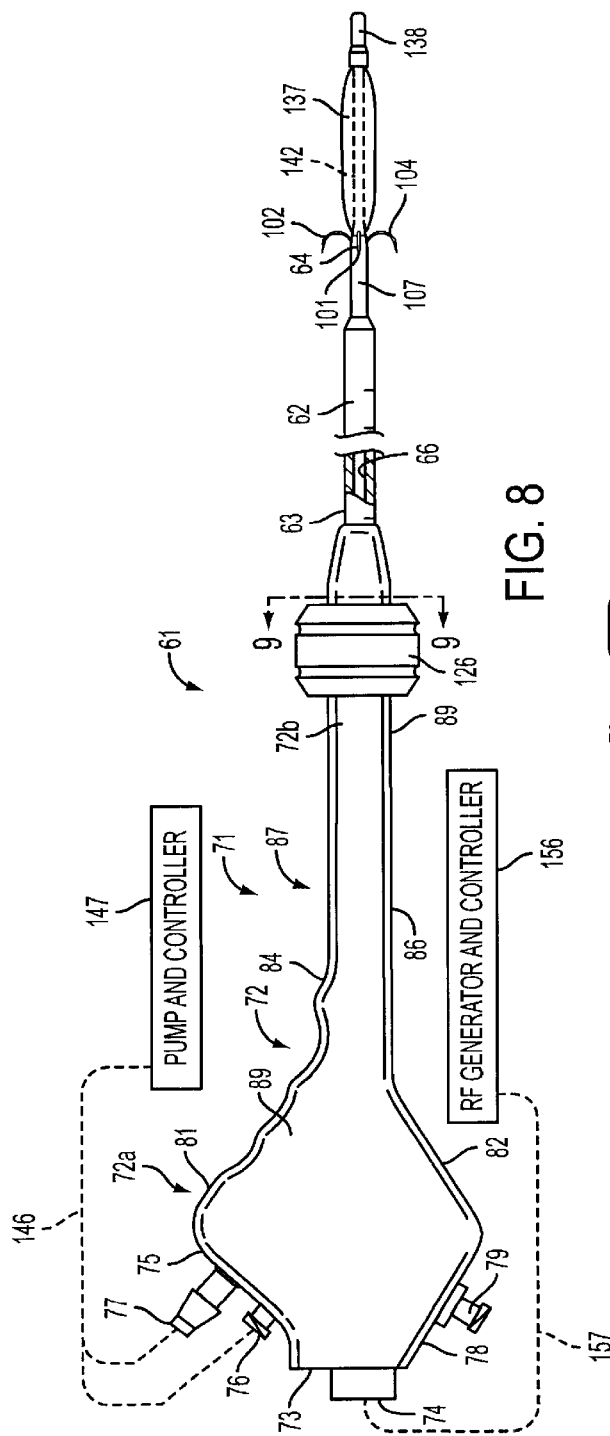
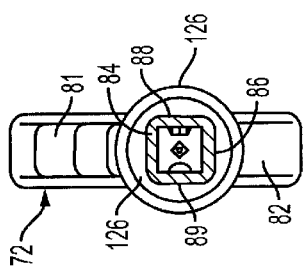
FIG. 8
FIG. 9

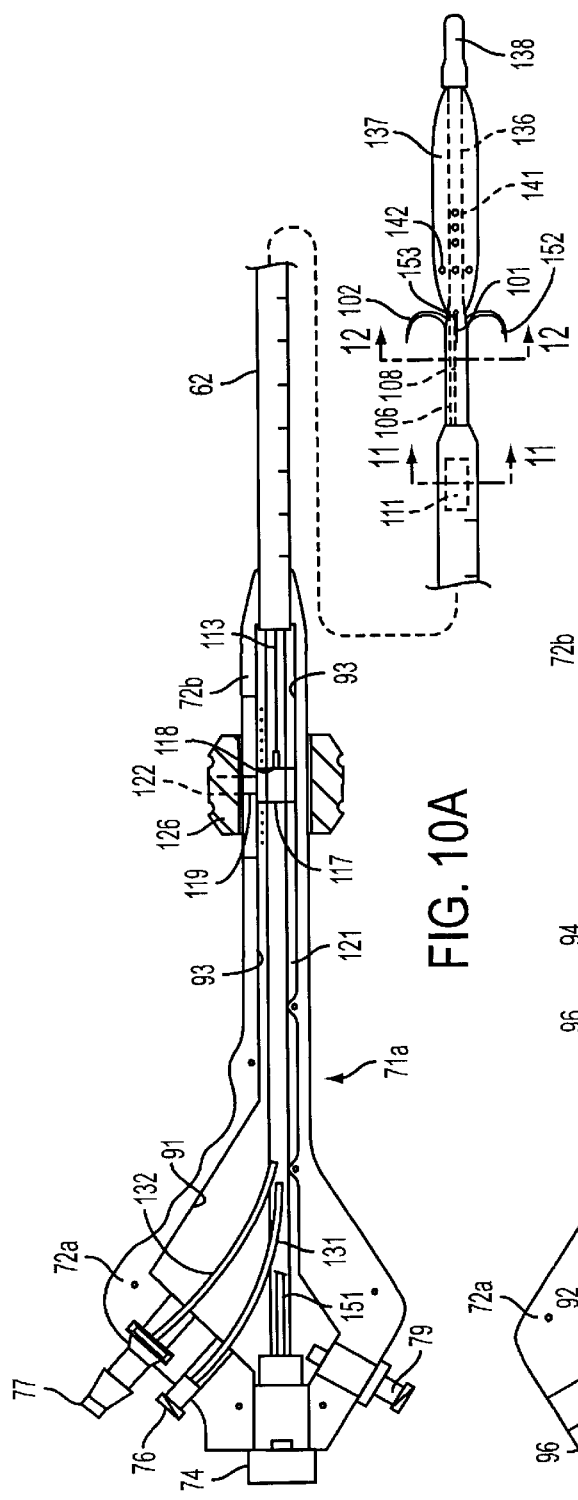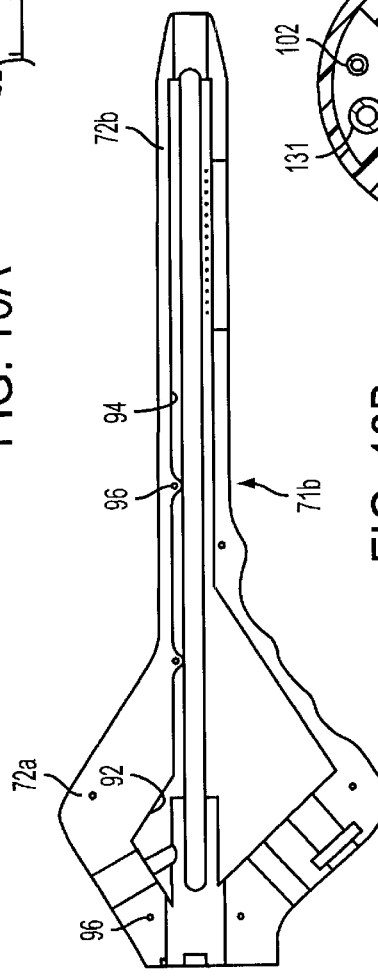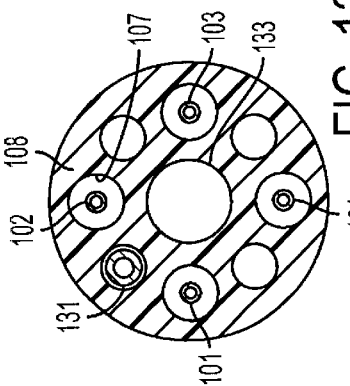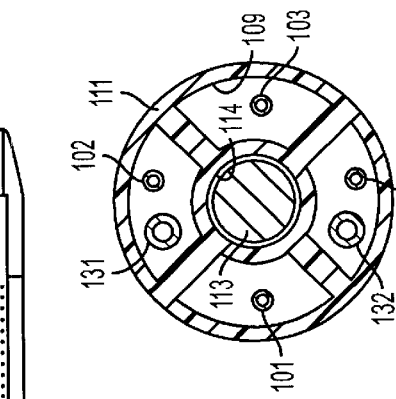

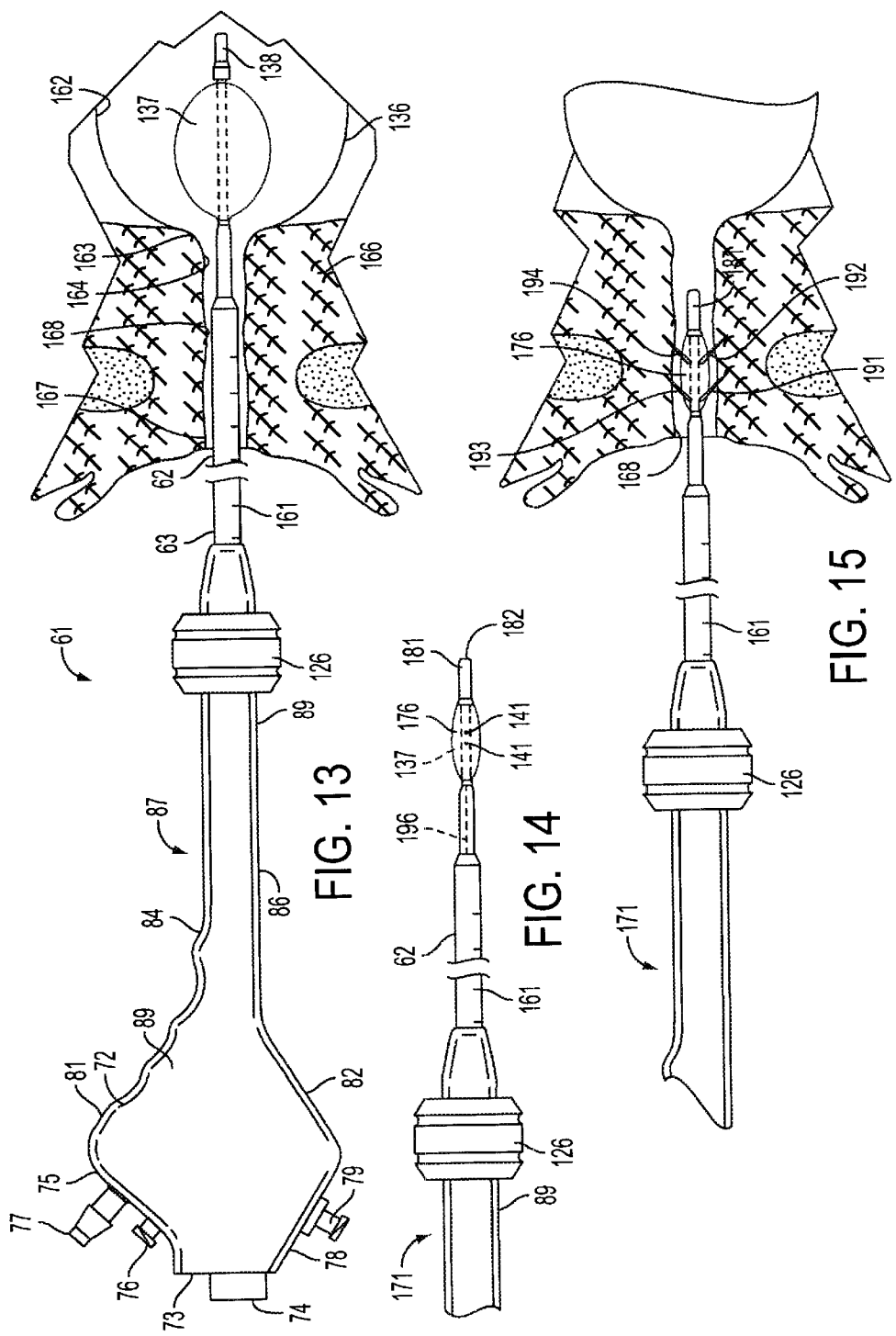

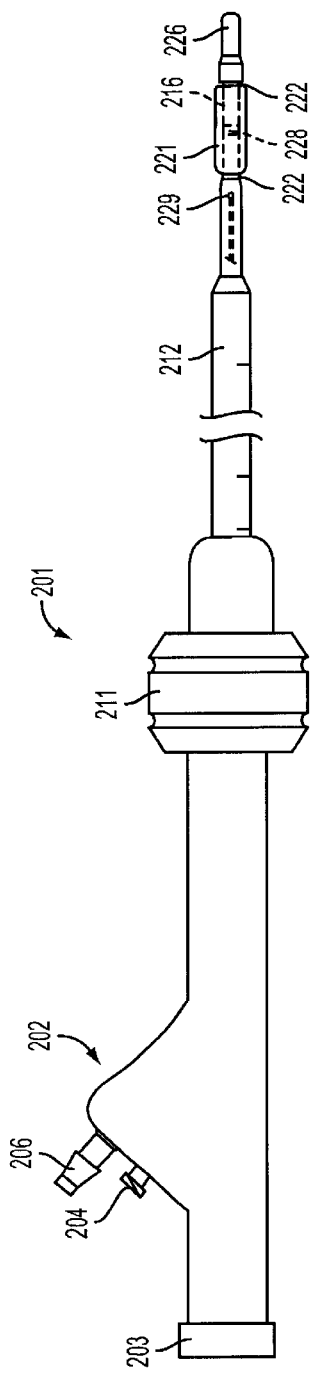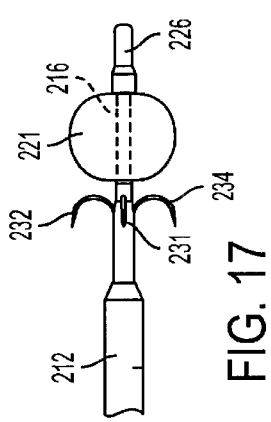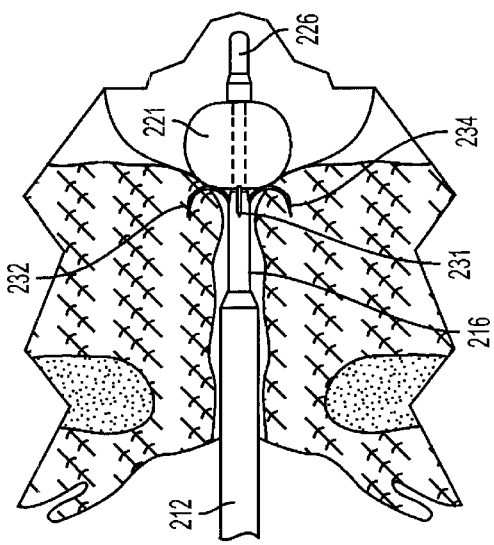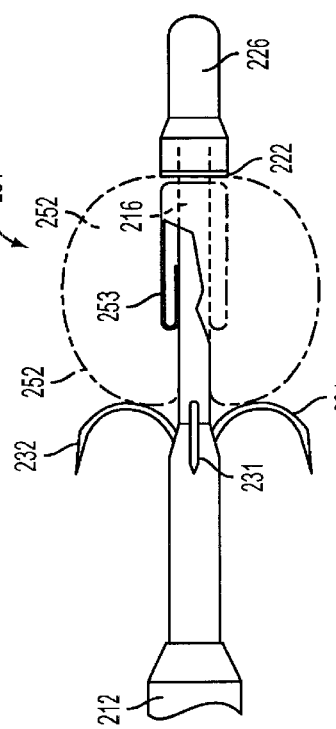
FIG. 16
FIG. 17
FIG. 18
FIG. 19

APPARATUS AND METHOD FOR TREATING FEMALE URINARY INCONTINENCE

This invention relates to an apparatus and method for treating female urinary incontinence and more particularly in humans.

The term "urinary incontinence" refers to an involuntary leakage of urine. Urine is released from the body in an uncontrolled manner from the bladder. The lack of bladder motility during activities is central to urinary incontinence. Furthermore, there is a small region of circular muscle surrounding the middle portion of the urethra in the female called the "urethral sphincter". This sphincter participates in the controlled release of urine from the bladder. If the bladder becomes too immobile or if the urinary sphincter or any part of the urinary system malfunctions, the result may be urinary incontinence. Urinary incontinence can generally be characterized into two types, one of which is called "stress incontinence" and the other "urge incontinence". Stress incontinence refers to involuntary loss of urine during coughing, laughing, sneezing, jogging or other physical activity that causes a sufficient increase in intra-abdominal pressure. Urge incontinence refers to the involuntary loss of urine due to unwanted bladder contraction that is associated with a strong uncontrollable desire to urinate. "Mixed incontinence" refers to a combination of both urge and stress incontinence. Heretofore many different types of treatment have been utilized to treat female urinary incontinence including surgical procedures which have included the injection of collagen or other material into the tissue surrounding the bladder outlet. In addition, drug therapy also has been utilized as for example drugs to treat the detrusor muscle which is a bladder wall muscle responsible for contracting and emptying the bladder without relaxing the outlet of the bladder. All of these procedures have drawbacks and also are relatively expensive. There is therefore a need for a new and improved apparatus and method for treatment of female urinary incontinence.

In general, it is an object of the present invention to provide an apparatus and method for treating female urinary incontinence which utilizes radio frequency energy for treating the urinary tract.

Another object of the invention is to provide an apparatus and method of the above character which includes a bladder outlet remodeling device and use thereof.

Another object of the invention is to provide an apparatus and method of the above character which includes a urethral sphincter remodeling device and use thereof.

Another object of the invention is to provide an apparatus and method of the above character which includes a catheter or probe with an inflatable elastomeric balloon on its distal extremity.

Another object of the invention is to provide an apparatus and method of the above character which includes an introducer and sheath particularly adapted for use in the urethra and for receiving the bladder and urethral sphincter remodeling devices.

Another object of the invention is to provide an apparatus and method of the above character which avoids major surgery and does not require surgical incisions so there is no disfiguring external scarring.

Another object of the invention is to provide an apparatus and method in which cooling liquid is provided during the procedure to minimize damage to the mucosa of the urethra.

Another object of the invention is to provide an apparatus and method of the above character which can be performed as an out-patient procedure.

Another object of the invention is to provide an apparatus and method of the above character in which only a local or regional anaesthesia is utilized.

Another object of the invention is to provide an apparatus and method of the above character which permits rapid treatment time.

Another object of the invention is to provide an apparatus and method of the above character in which there is minimal postoperative discomfort.

Another object of the invention is to provide an apparatus and method of the above character in which there is minimal or no postoperative bleeding.

Additional objects and features of the invention will appear from the following description in which the preferred embodiments are set forth in detail in conjunction with the accompanying drawings.

FIG. 1 is a side elevational view of an introducer used as a part of the apparatus for treating female urinary incontinence.

FIG. 2 is a side elevational view of a sheath incorporating the present invention which is utilized as a part of the apparatus of the present invention.

FIG. 3 is an enlarged sectional view of the proximal extremity of the sheath shown in FIG. 2 and particularly showing the valve housing.

FIG. 4 is a cross-sectional view taken along the line 4—4 of FIG. 3.

FIG. 5 is a cross-sectional view taken along the line 5—5 of FIG. 3.

FIG. 6 is a cross-sectional view taken along the line 6—6 of FIG. 3.

FIG. 7 is a side-elevational view of an assembly of the introducer and the sheath showing the manner in which the assembly is used for introduction into the urinary tract.

FIG. 8 is a side-elevational view of a bladder outlet remodeling device incorporating the present invention utilized in the apparatus of the present invention and including a radio frequency generator and controller and an irrigation pump and controller.

FIG. 9 is a cross-sectional view taken along the line 9—9 of FIG. 8.

FIG. 10A is a side-elevational view of the device shown in FIG. 8 split apart to show the two-part handle and showing a side-elevational view of one part of the handle and FIG. 10B showing the other part of the housing.

FIG. 11 is a cross-sectional view of the 5-lumen block used in the device shown in FIG. 8.

FIG. 12 is a cross-sectional view of the 9-lumen block used in the device shown in FIG. 8.

FIG. 13 is a diagrammatic view showing the manner in which the bladder remodeling device is utilized in treating the bladder outlet of a patient in accordance with the present invention.

FIG. 14 is a side elevational view of a urethral sphincter remodeling device incorporating the present invention and forming a part of the apparatus.

FIG. 15 is a diagrammatic illustration showing the manner in which the device in FIG. 14 is utilized for treating the urethral sphincter muscle in accordance with the present invention.

FIG. 16 is a side elevational view of a device incorporating the present invention and forming a part of the apparatus which includes an inflatable elastomeric balloon on the distal extremity which can be utilized for treating the bladder outlet of a patient showing the balloon reinflated.

FIG. 17 is a partial side elevational view of the device shown in FIG. 16 showing the elastomeric balloon in an expanded condition with the needle electrodes in a position with the needle electrodes out of contact with the elastomeric balloon.

FIG. 18 is a view similar to FIG. 17 but showing the device with the needle electrodes in contact with the elastomeric balloon during a bladder outlet remodeling procedure.

FIG. 19 is another embodiment of a device incorporating the present invention similar to that shown in FIG. 16 but showing a different elastomeric balloon.

In general, the apparatus of the present invention includes an introducer, an introducer sheath and a remodeling device. The remodeling device can either be a bladder outlet remodeling device or alternatively a urethral sphincter remodeling device where typically a patient may require use of only one of the devices. However, on occasion the condition of the patient may warrant treatment with both of the remodeling device in the attempt to eliminate or minimize urinary incontinence. The remodeling devices have an elongate tubular element or probe having a lumen extending from the proximal extremity to the distal extremity. A handle is secured to the proximal extremity of the probe and is adapted to be grasped by the human hand. A plurality of needle electrodes are carried by the distal extremity of the probe and are movable between retracted and extended positions and in a retracted position are disposed within the confines of the profile of the probe and in an extended position extending sidewise beyond the profile of the probe. Means is provided for supplying radio frequency energy to the needle electrodes when they are in an extended position to treat the desired tissue in the urinary tract. In the treatment of the bladder outlet, the electrodes are introduced into the musculature of the bladder outlet and in the treatment of the urethral sphincter muscle, the needle electrodes are introduced into the urethral sphincter muscle at predetermined energy levels for predetermined times. The treatment is closely monitored by temperature sensors. The procedure is utilized to reduce the size of the bladder outlet by use of the bladder outlet remodeling device and to shrink the urethral sphincter muscle by the use of the urethral sphincter remodeling device.

More in particular, the apparatus of the present invention for treatment of female urinary incontinence is comprised of a plurality of components which include an introducer 21. The introducer 21 is comprised of a semi-rigid member 22 formed of a suitable medical grade plastic and having a diameter ranging from 18 to 23 French and having a length ranging from 12 to 20 cm. The member is provided with proximal and distal extremities 23 and 24. A soft slightly tapered tip 26 formed of a suitable material such as a medical grade plastic is bonded to the distal extremity 24 by suitable means such as an adhesive or by the use of heat. The tip 26 is provided with a rounded distal surface 27 to minimize damage to the mucosa of the urethra.

The introducer 21 is used in conjunction with a sheath 31 as shown in FIG. 2 which also forms a part of the apparatus of the present invention. The sheath 31 is formed of an elongate tubular member 32 of a suitable medical grade plastic. The member 32 is provided with proximal and distal extremities 33 and 34 and has a lumen 36 extending from the proximal extremity 33 to the distal extremity 34. The lumen 36 is sized so that it can receive the introducer 21. Thus the member can have an outside diameter of 25 to 28 French and having a wall thickness of 0.01"~0.050". Sealing means 37 is carried by the proximal extremity 33 and includes a gasket seal 38 secured to the proximal extremity 33 by suitable means such as an adhesive (not shown). The gasket seal 38 can be formed of a suitable material such as a silicone rubber having a durometer Shore hardness ranging from 30 to 75. However, if desired, suitable medical grade plastic can be utilized. As shown particularly in FIG. 3, the tapered gasket seal 38 can be tapered inwardly and proximally so that its proximal most extremity has a diameter which is slightly less than the inside diameter of the lumen 36 so that a good sealing engagement will be made with the introducer 21 when it extends therethrough as hereinafter described.

The sealing means 37 also includes a cylindrical valve housing 41 mounted over the gasket seal 38 and on the proximal extremity 33 of the elongate tubular member 32 as shown in FIGS. 2 and 3. The housing 41 is formed by a rigid cylindrical member 42 formed of a suitable material such as medical grade plastic and which has one end open and which has the other end closed by a wall 43 having an opening 44 therein. A flexible liner or support member 46 is provided within the cylindrical member 42 and also can be formed of a suitable plastic material. It is provided with a lumen 47 into which the gasket seal 38 extends and opens into a cylindrical recess 48. First and second disc-shaped elements 51 and 52 are provided and are sandwiched between the wall 43 and the liner or support 46 and overlie the recess 48. The element 51 as shown in FIG. 4 is provided with two elongate slits 53 and 54 extending at right angles to each other and extending across a major portion of the disc-shaped element 51. Similarly as shown in FIG. 5, the disc-shaped element 52 is provided with elongate slits 56 and 57 also extending at right angles to each other. The elements 51 and 52 are positioned so that one set of slits is offset by an angle significantly less than 90° and preferably approximately 45° with respect to the other slits. Thus it can be seen that within the cylindrical valve housing 41 there are provided three seals of which 51 and 52 form first and second disc-like seals and the gasket seal 38 provides a third gasket-type seal, the combination of which is particularly desirable to form air- and fluid-tight seals between the sheath 31 and the introducer 21 for a purpose hereinafter described.

The introducer 21 is inserted into the sheath 31 as shown in FIG. 7 so that it can be utilized as an assembly 59 as hereinafter described.

The apparatus of the present invention also includes a bladder outlet remodeling device 61 of the type shown in FIG. 8 of the drawings. The device comprises a semi-rigid elongate tubular member or shaft 62 formed of a suitable grade medical plastic having a suitable diameter as for example ranging from 18 to 25 French and having a length ranging from 5 to 10 cm. It has proximal and distal extremities 63 and 64 with a lumen 66 extending from the proximal extremity to the distal extremity.

A handle 71 sized so as to be adapted to be grasped by the human hand is mounted on the proximal extremity 63 of the tubular member 62 for supporting the tubular member 62. The handle 71 is formed of a body 72 of a suitable rigid medical grade plastic. The body 72 has a proximal enlarged portion 72a which is generally square in side elevation and an elongate extension portion 72b. The proximal enlarged portion 72a is provided with a rear surface 73 through which an electrical connector 74 extends. It is also provided with a generally upwardly inclined surface 75 extending upwardly and distally from the rear surface 73 and carries a fluid-in port 76 and a fluid-out port 77. The portion 72a is also provided with a surface 78 which extends downwardly and distally from the rear surface 73 and carries an auxiliary port 79. The portion 72a is also provided with additional inclined surfaces 81 and 82 which extend downwardly and distally and upwardly and distally from the surfaces 75 and 78, respectively, which adjoin spaced-apart parallel top and bottom surfaces 84 and 86 of the elongate extension portion. The surfaces 84 and 86 adjoin spaced-apart parallel side surfaces 88 and 89 of the elongate extension 72b. The side surfaces 88 and 89 also form the sides of the body 72.

As shown in FIGS. 10A and 10B, the handle 71 is formed in two parts 71a and 71b with recesses 91 and 92 formed in the proximal portion 72a and with elongate recesses 93 and 94 being provided in the elongate extension 72b. The two parts 71a and 71b on the handle 71 can be fastened together by suitable means such as screws (not shown) positioned in holes 96 or ultrasonic bonding.

A plurality of needle electrodes 101–104 which are sharpened at their distal extremities are carried by the distal extremity of the tubular member 62. The needle electrodes are formed of a suitable medical grade material but in accordance with the present invention it is desirable to form them of a material which can assume a preformed memory when free as for example a nickel-titanium alloy which can be either a shape memory type or a superelastic type so that when free they will curve outwardly and downwardly to provide a fishhook-like configuration as shown in FIGS. 8 and 10A as hereinafter described. The needle electrodes 101–104 are disposed in suitable angular positions as for example spaced circumferentially in a single plane 90° apart. This is accomplished by slidably mounting the needle electrodes 101–104 in a plurality of small stainless steel hypotubes 106 as for example four of which are fixedly mounted by suitable means such as an adhesive (not shown) in four 90° spaced-apart lumens 107 in fixed positions in a nine-lumen Pebax block 108. This Pebax block 108 is mounted in a fixed position in the distal extremity 64 of the tubular member 62 by a suitable means such as an adhesive (not shown). The four needle electrodes 101–104 extend proximally through the hypotubes 106 and are mounted in fixed positions by suitable means such as an adhesive (not shown) in four lumens 109 spaced 90° apart in a five-lumen Pebax block 111 which is slidably mounted within the tubular member 62. A rigid elongate push-pull slide element 113 formed of a suitable material such as stainless steel has its distal extremity mounted in a fixed position in a centrally disposed lumen 114 of block 111 and extends proximally from the block 111 and into the recesses 93 and 94 of the elongate extension 87. A length of hypotube 117 is crimped onto the proximal extremity of the slide element 113. The proximal extremity of the slide element 113 is bent at right angles thereto so that the slide element 113 cannot escape from the crimped-on hypotube 117. A slider block 118 is secured onto the crimped-on hypotube 117 and is adapted to travel in the recesses 93 and 94 provided in the elongate extension 87. The slider block 118 is provided with an outwardly extending protrusion 119 which extends through an elongate slot 121 provided in the elongate extension 87. A cylindrical push-pull knob 126 is slidably mounted on the exterior of the elongate extension portion 72a and is secured to the protrusion 119 by a suitable means such as screw 122. By movement of the push knob 126 longitudinally of the elongate extension 87 by the hand grasping the handle, the needle electrodes 101–104 can be moved between extended and retracted positions in the hypotubes 106 for purposes hereinafter described by advancing the block 111 in the tubular member 62.

Means is provided for supplying a cooling liquid from the shaft 62 so that it is discharged in the vicinity of the needle electrodes 101–104 and more particularly into contact with the tissue being treated by the needle electrodes 101–104 and consists of tubing 131 connected to the fluid-in fitting 76 and tubing 132 connected to the fluid-out fitting 77. Tubing 131 and tubing 132 extend distally through the elongate extension 87 and into the lumen 66 of the tubular member 62. Tubing 131 and tubing 132 extend distally through the block 111 with tubing 132 terminating at block 108 and being placed in communication with a return lumen 133 in block 108. Tubing 131 continues through block 108 and opens into a tubular member 136 mounted on the block 108 and extending distally therefrom.

Means is mounted on the distal extremity of the shaft 62 which can serve as expandable anchoring means and is shown in the form of an inflatable balloon 137 mounted over the member 136. The proximal end of the balloon 137 is bonded to the block 108 to form a liquid- and air-tight seal with respect thereto and with the distal end of the balloon 137 is bonded near the distal end of the tube 136 by a soft flexible tip 138 formed of a suitable plastic such as polyurethane to prevent peeling-off of the distal extremity of the balloon from the shaft 62. The balloon can have a suitable length as for example 4 to 6 cm. The balloon can be formed of suitable materials such as polyethylene, latex, Pebax and Nylon. When formed of polyethylene, Pebax and Nylon it has a predetermined size. When formed of an elastomer the size is not predetermined and its size is indeterminate.

The tube 136 is provided with openings 141 therein within the balloon 137 which are in communication with the liquid in tubing 131 so that the liquid can be supplied to the interior of the balloon 137 to insufflate or inflate the same. Although the balloon 137 is preferably inflated with a liquid which is substantially incompressible so that so that the size of the insufflated balloon can be determined by the amount of liquid introduced, a fluid including a gas as well as a liquid can be utilized for insufflating the balloon albeit with less accuracy with respect to the inflated diameter of the balloon when an elastomeric material is used for the balloon.

In accordance with the present invention the balloon 137 is provided with a plurality of circumferentially spaced-apart small openings 142 through which the cooling liquid introduced into the balloon 137 through the tubing 131 can escape and be discharged in the vicinity of the needle electrodes 101–104 to cool the tissue being treated as hereinafter described. The cooling liquid after it has performed its function is aspirated through a central return lumen 133 in block 108. This lumen 133 is in communication with tubing 132 to the fluid-out fitting 77.

The fluid-in fitting 76 and the fluid-out fitting 77 are connected by tubing 146 (shown schematically) to an irrigation pump and controller 147 which is used for supplying a cooling liquid such as room temperature water to fluid-in fitting 76 and for aspirating the liquid after it has been used through the fluid-out fitting 77.

A plurality of insulated wires 151 are provided which are connected to the connector 74 with slack being provided in the same within the recesses 91 and 92. The wires 151 extend distally through the elongate extension through the lumen 66 of the tubular member 62 and through lumens in the blocks 108 and 111. For example four impedance wires can be provided which are soldered to the four hypotubes 106. The four thermocouple wires extend through the hollow needles 101–104 and are connected to thermocouples 152 mounted in the sharpened tips for measuring needle-tip temperatures. Four additional thermocouples 153 are mounted on the probe 62 immediately adjacent the proximal extremity of the balloon for measuring surface temperatures.

The electrical connector 74 as shown is connected to an RF generator and controller 156 by a cable 157 as shown schematically.

To facilitate use of the bladder outlet remodeling device 61, a plurality of longitudinally spaced-apart markings 161 are provided on the tubular member or probe 62 which forms the shaft for the device to make it easy to ascertain how far the distal extremity of the device has been inserted into the urethra in performing a procedure.

Let it be assumed that a patient is to be treated for female urinary incontinence in connection with use of the present apparatus in performing the method of the present invention. The patient is prepared for the procedure in a conventional manner and is placed typically in a lithotomy position. The patient may be given a caudal or a local anaesthesia. A grounding pad is placed on a thigh or buttock of the patient and the connector 74 of the bladder outlet remodeling device 61 is connected to the radio frequency generator and controller 156 at an appropriate point in the procedure.

As shown in FIG. 13, the female patient as is well known from human anatomy has a bladder 162 opening through a bladder neck outlet 163 into the urethra 164 formed within tissue 166 surrounding the urethra. The urethra 164 runs above the anterior vaginal wall and empties through the urinary meatus 167. The urethra 164 is surrounded by a urinary sphincter 168 positioned approximately one-third to midway the length of the urethra. A Foley catheter is placed to initially empty the bladder and then a set amount of liquid preferably in the range of 400–500 cc of sterile water is introduced into the bladder through the Foley catheter so that the bladder 162 is partially distended to inhibit the electrode needles of the present invention from disturbing the mucosa.

Assuming that the apparatus of the present invention has been supplied as a kit to the physician, the physician removes the introducer 21 and then places the introducer 21 into the sheath 31 by first introducing the proximal extremity 23 of the introducer 21 through the distal extremity 34 of the sheath 31 so that the introducer first passes through the gasket seal 38 and then thereafter through the two disc-shaped elements 51 and 52 and protrudes therefrom as shown in FIG. 7 to provide the assembly 59. The introducer 21 and the sheath 31 are then covered with a lubricant jelly to ensure that there is lubricant jelly over both the introducer 21 and the sheath 31. The introducer and sheath assembly 59 as shown in FIG. 7 is then introduced as an assembly through the urinary meatus 167 into the urethra 164 of the patient with the soft tip 26 of the introducer 21 guiding the way. This assembly 59 under direct vision of the physician is passed through the bladder neck outlet 163 so that the distal extremity of the introducer extends transurethrally into the bladder. As soon as this has been accomplished, the introducer 21 can be removed leaving the sheath 31 in place with its distal extremity extending into the bladder. Because of the relatively large size of the introducer and the remodeling devices hereinafter described, it is important to provide a good seal on the sheath. Thus even though relatively large devices as for example 18 to 25 French in diameter pass through the cylindrical valve housing 41, no appreciable urine or other liquid escapes from the sheath 31.

At this point in time, the tip of the distal extremity 34 of the sheath 31 is above the proximal urethral orifice in the base of the bladder with the bladder still being distended and with the liquid not escaping from the bladder because of the seals provided in the cylindrical valve housing 41. The bladder outlet remodeling device 61 is now taken from the kit and a lubricant jelly is placed on the tip and onto the balloon 137 and onto the probe or shaft formed by the tubular member 62. Thereafter, the tip 138 and the balloon 137 are carefully introduced into the sheath 31 and advanced into the sheath for a predetermined distance as determined by the markings 161. Typically because of the known length of 2½ to 4 cm of the urethra 164 before the bladder 162, the device is introduced for a distance of approximately 6 cm to ensure that the balloon 137 is disposed within the bladder. Thereafter, the sheath 31 is pulled back so that it is completely out of the bladder 162 but is still surrounding the shaft or tubular member 62 of the remodeling device 61.

If not accomplished previously, a ground is placed on the thigh or buttock of the patient and the cable 157 from the RF generator 156 is connected to the connector 74. The irrigation pump 147 is connected to the fluid-in port 76 and fluid-out port 77. The irrigation pump 147 is primed to cause the irrigation fluid, which typically can be tap water at room temperature, to enter the fluid-in port 76 and eventually pass out the fluid-out port 77. Priming by the irrigation pump 147 forces all the air out of the system and in turn also forces any air present to the top of the bladder. Captured air in this location is of no consequence. While priming is occurring, balloon 137 is insufflated with the irrigation fluid or irrigant. When the balloon is substantially filled, the irrigant begins flowing out of the holes 142 of the balloon 137. If the patient feels discomfort at this time, the bladder can be palpated and liquid aspirated from the bladder in a conventional manner.

Typically the irrigation pump and controller 147 has three different flow rates with flow rate 1 being a low flow rate, with flow rate 2 being a medium flow rate and with flow rate 3 being a high flow rate. These various flow rates can be selected in accordance with the needs of the procedure being performed. Typically during bladder remodeling flow rate 2 is utilized. Priming is normally accomplished at the high flow rate 3, after which the balloon is filled at the high flow rate. After approximately 15 seconds have elapsed during rapid filling of the balloon, the irrigation pump and controller 147 is switched to flow rate 2.

In this first stage after priming, the balloon 137 as being insufflated is expanded and positions itself within the bladder outlet. The room temperature water which is utilized for inflating the balloon becomes warmed to the patient's own temperature in the bladder.

As soon as the balloon 137 has been expanded and positioned within the bladder, the physician grasps the handle 71 of the device 61 with one hand and with the thumb or one or more fingers of the same hand pushes the push knob 126 forwardly to cause the needles 101–104 to be advanced from their retracted positions and to move distally and sidewise beyond the outer cylindrical profile of the tubular member 62 into the tissue of the bladder neck 161. The needle electrodes 101–104 because of their formation of a nickel-titanium alloy as hereinbefore explained have a memory which causes them when free to bend in a fishhook-shaped curve proximally and then distally to extend through nearly 180°. This memory effect is enhanced by warming of the needle electrodes 101–104 by the liquid in the bladder of the patient. As hereinbefore explained, since four needles are provided in the present arrangement, the needles enter at four circumferentially spaced apart locations in a single plane at level spaced approximately 90° apart as shown in FIG. 13. At this level 1, the needle electrodes 101–104 are proximal of the balloon 137 and their positioning is not affected by the balloon 137. The needle electrodes enter approximately one centimeter into the tissue and curve proximally a distance of approximately 18 millimeters.

As soon as the needles 101–104 have been properly positioned, radio frequency energy is supplied from the RF generator and controller 156 under the control of the generator and controller 156. As is well known to those skilled in the art, such a generator can provide impedance readings which give an indication of whether or not the needle electrodes 101–104 have been properly located or positioned within the tissue to provide sufficient penetration into the tissue. While liquid is still being introduced at flow rate 2 from the irrigation pump 147, radio frequency energy is supplied to the needle electrodes at a power level ranging from 6 to 50 watts for a period of time ranging from 60 to 90 seconds to achieve approximately an 80° C. temperature in the tissue being treated while the overlying mucosal tissue is preserved by the cooling liquid flow to treat the detrusor musculature of the bladder outlet. In accordance with the present invention it is desirable not to reach a temperature of 100° C. Therefore the RF generator 156 utilizing the information supplied from the thermocouples 152 and 153 will automatically turn off the RF generator 156 when the temperature reaches a set temperature as for example as high as 95° C.

As soon as this first RF treatment has been completed, the radio frequency energy is turned off and the knob 126 is retracted to withdraw the needle electrodes 101–104 into their retracted positions so that their distal extremities are within the confines of the outer cylindrical profile of the shaft 62. As soon as this has been accomplished, the device can be advanced several centimeters inwardly of the bladder outlet into the expanded bladder 162 and rotated a predetermined angle as for example 22½° if two treatments are contemplated or 15° if three treatments are contemplated. As soon as the needles 101–104 have been rotated to the desired angle, the handle 71 is pulled to seat the balloon 137 in the bladder neck after which the needles 101–104 are advanced in the same manner hereinbefore described into the tissue at level 1 and thereafter radio frequency energy supplied with the same amount of power and timing as hereinbefore described. If it is believed that a further treatment is indicated, the needles 101–104 are again retracted by retracting the knob 126 to retract the needles 101–104, rotating the device 61 as for example 15°, seating the balloon 137 and the needles 101–104 reinserted at level 1 and another radio frequency energy treatment given to the tissue. During this entire procedure, irrigation liquid is being introduced through the balloon.

In each of these treatments it can be seen that the balloon 137 is moved into the bladder 162 and then rotated and then re-anchored and the needles redeployed in each treatment. In this way, the treatment of the tissue is always approximately at the same level in the bladder neck outlet 163 so that the treatments are in a single plane.

From the foregoing it can be seen that the bladder neck outlet treatment procedure in accordance with the present invention involves at least one and preferably two and possibly as many as three treatments in the same plane which are accomplished by repeatedly anchoring the balloon in the bladder neck outlet 163 of the bladder 162 which empties into the urethra 164. The needle electrodes 101–104 are then repeatedly advanced into the tissue of the bladder neck and an RF treatment is applied. As can be seen, all two or three of these treatments are accomplished in the same plane of the bladder neck outlet 163 which also can be considered to be a lower or lowest plane for RF treatments in the bladder neck outlet 163.

With some patients it may be desirable to also perform RF treatments in one or more higher planes or levels distal of the lowermost plane. Let it be assumed that it is desired to accomplish one or more such additional treatments. When this is to be accomplished, the needle electrodes 101–104 are again retracted. After they have been retracted, the balloon 137 is moved distally or upwardly into the bladder 162 for example a distance of approximately 4 cm into the distended bladder. With the balloon 137 in this position, the electrodes 101–104 are again advanced. As soon as the needle electrodes 101–104 have been advanced, the handle 71 is pulled proximally to seat the needle electrodes 101–104, which are in the form of non-barbed fish hooks, are seated in the tissue in a plane at level 2. In this plane the needle electrodes 101–104 are adjacent the balloon 137 but are not supported by the balloon 137. The needle electrodes 101–104 penetrate the tissue to a depth of approximately one centimeter and extend proximally a distance of approximately 24 millimeters. This seating can be readily felt by the hand of the physician holding the handle 71. Radio frequency energy is then introduced through the needle electrodes 101–104 in the same manner as the previous RF treatments.

Assuming that one or two additional treatments are desired in this higher plane or level 2, the needle electrodes 101–104 are retracted, the handle 71 with the balloon 137 thereon is rotated by an appropriate angle as for example 22½° or approximately 15°. The needle electrodes 101–104 are then advanced and then seated by pulling on the handle 71. This seating is followed by the RF treatment. If another treatment is desired, the handle 71 and the balloon 137 carried thereby are rotated by the appropriate amount and then advanced and seated followed by an RF treatment to complete the procedure in that plane.

If it is desired to provide RF treatment in the bladder neck outlet 163 at a still higher plane as for example a third plane or level 3, the balloon 137 is advanced further upwardly or distally into the bladder 162 to define another plane for treatment with the needle electrodes 101–104. In this plane the needle electrodes 101–104 are supported by the balloon 137. The needle electrodes 101–104 extend into the tissue by approximately one centimeter and extend proximally approximately 30 millimeters. The treatment can be accommodated in the same manner as in the second plane at level 2 by advancing the needle electrodes 101–104 and applying an RF treatment and withdrawing the needles followed by rotation so that sites in the tissue are treated at the various angles to provide a third plane of treatment.

Thus, there can be three sets of ablations, the highest set being proximally or higher in the bladder neck outlet 163 and a middle set at an intermediate elevation within the bladder neck outlet 163 and the lowest set which is at the beginning of the urethra or urethral tract 164. In the first level of treatment, the needle electrodes 101–104 are penetrating the detrusor muscle which lies below a sub-mucosal collagen layer. The detrusor muscle is the thickest in this small region of the bladder neck 161. The second and third levels of treatment also enter the detrusor muscle. The detrusor muscle, however, thins out proximally in the bladder and for that reason it is relatively ineffective to provide more than three levels of treatment of the type hereinbefore described.

During the RF treatments hereinbefore described, a cooling liquid is continuously supplied from the holes 142 in the balloon 137 to cool the mucosa to prevent the mucosal temperature from reaching dangerous levels that would leave a scar. In addition a target temperature is set to stay below 50° C. which is ascertained by the thermocouples 152 and 153. If any needle temperature or surface temperature exceeds this temperature of 50° C., the RF generator 156 is turned off.

Let it be assumed that the RF treatments in the bladder neck have been completed. With the bladder outlet remodeling device 61 still in place, the sheath 31 is advanced back into the bladder outlet. The balloon 137 is then deflated by disconnecting the tubing 146 and using a syringe on the aspiration port 77. When the balloon 137 has been deflated, the balloon is drawn back into the sheath 31. The remodeling device 61 may then be removed with the sheath 31 to complete the procedure.

In a small but significant minority of patients urinary incontinence may be occurring for additional reasons other than bladder outlet hypermotility. For example certain patients may have isolated urethral sphincter injuries or a combined urethral sphincter and bladder neck outlet disfunction. Such patients with sphincter muscle problems will -need the additional treatment hereinafter described, either by itself or in combination with the bladder outlet remodeling device 61. The urethral sphincter 168 circumferentially surrounds the urinary tract 163 and is disposed proximally from 1 to 1⅓ cm inwardly of a urethra 164 typically having a length of 3 to 4 cm in human women. In treating the urethral sphincter 168, a urethral sphincter remodeling device 171 is provided. This remodeling device 171 is similar in many respects to the bladder outlet remodeling device 61 and therefore for the common parts, reference can be made to the description of the bladder remodeling device 61. As shown in FIG. 14, the device 171 consists of a handle 71 substantially identical to the handle 71 hereinbefore described. The tubular member 62 forming the shaft or probe is also substantially identical to that hereinbefore described. However, rather than a balloon 137 being mounted on the tube 136, a porous resilient foam member 176 is mounted thereon. The member 176 is formed of a suitable material such as of a polyurethane foam. It can have a suitable dimension such as a diameter of 1 to 1½ cm and a length ranging from 1½ to 2½ and preferably 2 cm. Both ends of the member 176 can be rounded as shown. The porous foam member 176 is disposed over openings 141 provided in the tube 136 so that irrigation liquid supplied can readily pass through the porous foam member 176. A soft pliable tip 181 extends distally from the foam member 176 and has a rounded blunt end 182.

As in the bladder outlet remodeling device 61, four needle electrodes 191–194 are provided in the urethral sphincter remodeling device 171. They also can be formed of a nickel-titanium alloy. However, in this remodeling device 171, the needle electrodes 191–194 remain relatively straight and extend outwardly at an angle of approximately 60° from the longitudinal axis of the tube 136. These needle electrodes 191–194 are mounted in the same manner as the needle electrodes 101–104 in the bladder outlet remodeling device 61 and extend through small hypotubes 196 corresponding to the hypotubes 106, as shown in FIG. 10A. The hypotubes 196 differ from the hypotubes 117 in that rather than terminating proximal of the foam member 176, two of the four hypotubes extend at right angles to the axis of the first two hypotubes 196 and extend distally from the center of the foam member 176. Thus when the needle electrodes 191–194 are retracted they are disposed within the hypotubes 196 and are also covered by the foam member 176. When the needle electrodes, 191–194 are moved to the extended positions, they extend at approximately 60° angles and penetrate through the foam member to provide four needles in two sets of needles which are staggered circumferentially and longitudinally of the foam member 176.

Operation and use of the urethral sphincter remodeling device 171 may briefly be described as follows in conjunction with FIG. 15. Let it be assumed that with respect to the operation hereinbefore described with respect to the bladder outlet remodeling device 61 that it has been accomplished and the device 61 removed.

Before introducing the urethral sphincter remodeling device 171, the foam member 176 is initially soaked in water so that the sponge is evenly moistened throughout. A lubricant belly is then placed on the tip 181. The device 171 is passed under direct vision into the urethra 164 based on known lengths of urethras and the markings on the shaft 62. The foam member 176 is positioned so that it is disposed in the vicinity of the urethral sphincter approximately 1 to 1⅓ cm into the urethra 164 to hold the urethra 164 in a mildly distended position. The device 171 is then connected to the pump 147 by making a connection to the input port 76. Although it may not be necessary, a connection can also be made from the pump to the aspiration port 77. Aspiration may not be needed because the cooling liquid can flow directly out of the urethra.

At this time, the push knob 126 can be advanced to advance the circumferentially and longitudinally staggered needle electrodes 191–194 through the foam 176 and into the tissue of the urethral sphincter 168. The foam or sponge member 176 in addition to dispersing the cooling liquid over the mucosa to be penetrated also aids in the needles penetrating the tissue to a depth of approximately one-half centimeter by serving as a buttress without tenting of the mucosa or the underlying tissue of the urethral sphincter 168 with the urethra in its mildly distended position. With this buttressing action of the foam member 176 and also because of the 60° angle of needle penetration there is minimal tenting.

As soon as the needle electrodes 191–194 are deployed, radio frequency energy is supplied to the needle electrodes 191–194 from the RF generator 156 at appropriate power levels ranging from 1 to 50 watts, preferably 5 watts, for a period of time ranging from 30 seconds to 120 seconds, preferably approximately 60 seconds.

After this first treatment has been completed, the needles 191–194 are retracted by withdrawing the knob 126 to bring the needles 191–194 so that they are no longer exposed. Thereafter, one additional treatment is usually contemplated with the foam member 176 being moved in a craniocaudal plane. With the irrigation liquid continuously flowing, the electrode needles 191–194 are again advanced so that they extend beyond the profile of the shaft or tubular member 62 and beyond the profile of the foam member 176 to penetrate the tissue in the manner hereinbefore described. Radio frequency energy is again applied at the same power levels and for the same period of time. As soon as this has been completed, the needle electrodes 191–194 can be retracted by retracting the knob 126 after which the device 171 can be removed from the urethra to complete the procedure.

Another embodiment of a device 201 incorporating the present invention is shown in FIG. 16. As can be seen from the drawing, in many respects the device 201 is very similar to the device 61 hereinbefore described. It consists of a handle 202 provided with an electrical connector 203 corresponding to the electrical connector 74. It is also provided with a fluid-in irrigation port 204 corresponding to port 76 of device 61 and a balloon inflation-deflation port 206. The suction port 77 of device 61 has been omitted because it is optional. A push-pull knob 211 corresponding to the push-pull knob 126 is provided on the handle 202. A tubular member or shaft 212 corresponding to the tubular member 62 extends distally from the handle 202. A tubular element 216 is mounted on the tubular member 212 and is in communication with the lumen 133 in block 108 which is in communication with the balloon inflation-deflation port 204. In this embodiment of the invention, the expandable anchoring means takes the form of an elastomeric balloon 221 is mounted on the tubular element 216 with the proximal and distal extremities of the balloon 221 being secured to the tubular element 216 in a suitable manner such as tie-downs 222. The tie-downs 222 are in the form of plastic filaments formed of a suitable material such as Pebax which are tied over the ends of the balloon. Alternatively the tie-downs 222 can be formed by placing short lengths of tubing (not shown) over the ends of the balloon 221 and bonded in place by a suitable adhesive. It has been found that the use of such tie-downs 222 is very desirable because they prevent peeling off of the balloon 221 and elongation of the balloon. The tie-downs 222 also ensure that the proximal and distal extremities of the balloon 221 will remain firmly secured to the tubular element 216 and form air-tight and liquid-tight seals with respect thereto. A soft tip 226 is mounted on the distal extremity of the tubular element 216. A hole 228 is provided in the tubular element 216 and is provided for inflating and deflating the balloon 221. The size of the balloon is controlled by supplying a predetermined quantity of liquid to the balloon 221. For example a syringe containing 5 cc of water can be utilized for inflating the balloon utilizing the inlet port 204 and supplying the liquid through the hole 228 into the balloon to provide a balloon of the desired controlled size with the balloon having a predetermined diameter and a predetermined length with the length being determined by the spacing between the tie-downs 222 to provide a balloon 221 which is substantially spherical with flattened ends which also can be characterized as being apple-shaped. The diameter is determined by the quantity of liquid introduced into the balloon because the liquid is substantially incompressible. It should be appreciated that although a liquid is preferable for inflating the balloon 221, any fluid such as a gas may also be utilized if desired.

Rather than the cooling irrigation fluid being supplied into the interior of a balloon as disclosed in the device 61, the cooling liquid from the port 206 is supplied though tubing in the same manner as in the device 61 but with the cooling fluid passing through openings 229 on distal extremities of the tubular element 216 to cause the cooling liquid to be introduced into the vicinity of the needle electrodes 231–234 which are of the same type as the needle electrodes 101–104 hereinbefore described.

Operation and use of the device in conjunction with the apparatus and method hereinbefore described is very similar. The principal difference in the present device is the use of the elastomeric balloon which makes it possible to provide a balloon when constructed in the manner shown of a controlled diameter and a controlled length. By tying down the ends of the balloon it is possible to form a sphere with slightly flattened ends. At the same time it is possible to fix the plane at the proximal end of the balloon so that the spacing between the end of the balloon and the needle electrodes can be precisely determined. By knowing the length and by knowing the quantity of water being introduced, it is possible to precisely control the diameter of the balloon. The tie-downs on the ends of the balloon prevent the balloon from peeling off during inflation.

In utilizing the device 201 in bladder outlet remodeling procedures, the positioning of the needle electrodes 231–234 can be more precisely determined. For example as shown in FIG. 17, the needle electrodes 231 and 234 are proximal of the balloon 221 and therefore the balloon does not support the needle electrodes during entry into the tissue. However, as shown in FIG. 18, when the needle electrodes 231–234 are advanced further under the control of the push-pull member 211, they come into engagement with the spherical elastomeric balloon 221 so that the needle electrodes are firmly supported by the balloon to aid in achieving the desired penetration of tissue in the desired locations as for examples at levels 1, 2 and 3 hereinbefore described with respect to previous embodiments. Thus with the device 201 it is possible to achieve multiple levels of needle electrode penetration with different types of penetration being determined by the configuration of the balloon and its controlled size. The flattened ends of the spherical balloon make it possible to provide excellent support for the needle electrodes during deployment of the needle electrodes because of the configuration of the flattened ends of the spherical balloon 221. The depth of penetration of the needle electrodes 231–234 into the tissue can also be increased when the needle electrodes are in contact with the balloon 221 by introducing additional liquid into the balloon 221. The use of the cooling liquid in the vicinity of the needle electrodes can still be accomplished by the use of the device 201.

Still another embodiment of a device incorporating the present invention utilizing a modified elastomeric balloon is shown in FIG. 19 in which the device 251 in many respects is similar to the device shown in FIG. 16. The device 251 is shown in FIG. 19 and differs principally in that a different elastomeric balloon 252 has been provided in place of the elastomeric balloon 221. The distal extremity of the balloon is secured to the tubular element 216 by a tie-down 222 of the type hereinbefore described. The proximal extremity of the balloon 252 is provided with a fold 253 which extends inwardly by approximately one-third of the length of the balloon with the proximal extremity of the fold being secured to the member 216 by a suitable means such as an adhesive (not shown). As shown in dotted lines when the inflatable balloon 252 is inflated as hereinbefore described in connection with the embodiment shown in FIG. 16, it can be seen that the balloon 252 will be inflated evenly about its circumference and at the same time this is occurring, the proximal extremity will begin to unfold and move towards the needle electrodes 231–234 and engage the needle electrodes 231–234 to aid in causing the needles to penetrate the tissue of the bladder outlet as shown in dotted lines in FIG. 19. By adjusting the balloon inflation the distance between the balloon and the needle electrodes 231–234 can be adjusted to thereby adjust the depth of penetration of the needle electrodes 231–234 into the tissue. In addition, since the balloon 252 is anchored or seated in the bladder outlet, the regions of penetration by the needle electrodes 231 and 234 with respect to the bladder outlet also can be adjusted by adjustable inflation of the balloon 252.

It should be appreciated that although the device 201 as shown in FIG. 16 has been described principally in connection with female incontinence, a catheter or probe utilizing only the elastomeric spherical balloon with its flattened ends and controlled size in length and diameter can be utilized in other medical procedures as for example in the esophagus or in other openings in the human body.

Although different types of balloons have been described in connection with the devices of the present invention to be utilized as expandable anchoring means, it should be appreciated that different types of expandable anchors can be utilized. For example oval or spherical loops or baskets formed of a suitable shape memory material such as a nickel-titanium alloy can be utilized for such expandable anchors with the anchors being retractable and being deployed from a sheath carried by the distal extremity of the shaft of the device. Alternatively a plurality of hinged arms swingable between closed in-line positions and open expanded positions can be utilized under the control of a pull wire carried by the device.

From the foregoing, it can be seen that there has been provided a treatment for remodeling the urethral sphincter 166 by appropriate treatment of the middle portion of the urinary tract by treating in particular the higher and lower portions of the middle third by the two treatments hereinbefore described.

In connection with either or both of the remodeling treatments hereinbefore described in connection with the present invention, it may be necessary for the patient to be provided with a temporary indwelling Foley catheter with a leg bag for discharge to her home as an outpatient. In connection with the procedures, the patient may also be given short term antibiotics. The patient should be fully recovered within two weeks or less.

In connection with the foregoing procedures, as pointed out above, the temperature of each individual needle electrode is constantly being monitored to ensure that safe and effective treatment temperatures are not exceeded. In the event any needle exceeds the temperature safety limits, radio frequency power to that needle is terminated immediately without aborting the entire procedure.

In connection with the RF treatments, the tiny sites of treated muscle resorb, remodel and shrink over the ensuing weeks resulting in circumferential tightening or low mobilization of the bladder neck outlet and also of the urethral sphincter muscle resulting in a significant improvement in urinary continence.

The procedures of the present invention can typically be performed in an outpatient procedure with no hospital stay, making it possible to avoid major surgery. Only local or regional anaesthesia is required. There is minimal or no postoperative bleeding and there is minimal postoperative discomfort. There is no incision or external scarring.

What is claimed:

1. A device for use with a source of radio frequency energy and a source of cooling liquid for remodeling a treatment site within a female patient's urinary tract including a urethra and a bladder having a bladder neck outlet, the device comprising:
    an elongate tubular shaft having proximal and distal ends;
    an expandable member mounted adjacent to the distal end of the shaft, the expandable member having an expanded state when disposed within the bladder so that the expandable member engages the bladder neck outlet;
    a plurality of needle electrodes disposed within the shaft at a predetermined distance proximally of the expandable member, the plurality of needle electrodes adapted to be coupled to the source of RF energy and being selectively deployable from within the shaft at a treatment site defined in cooperation with the expandable member;
    a handle mounted on the proximal end of the shaft; and
    means carried by the handle and adapted to be coupled to the source of cooling liquid for supplying cooling liquid in the vicinity of the plurality of needle electrodes.

2. A device as in claim 1 further including temperature sensing thermocouples disposed in the plurality of needle electrodes.

3. A device as in claim 1 wherein the plurality of needle electrodes are formed of a nickel-titanium alloy.

4. A device as in claim 1 wherein the expandable member is a balloon.

5. A device as in claim 4 wherein the needle electrodes assume a curved shape when deployed.

6. A device as in claim 4 wherein the expandable member is secured to the distal end of the elongated shaft by an atraumatic tip.

7. A device as in claim 6 wherein the balloon when inflated has flattened ends.

8. Apparatus for remodeling a treatment site within the urinary tract of a female patient, the urinary tract including a urethra and a bladder having bladder neck outlet, the apparatus comprising:
    an elongated shaft having proximal and distal ends and a diameter adapted to be inserted within the urethra;
    a handle secured to the proximal end;
    a balloon disposed on the elongated shaft adjacent the distal end, the balloon adapted to be inflated in the bladder to a diameter sufficient to prevent retraction of the balloon through the bladder neck outlet into the urethra; and
    a plurality of needle electrodes disposed circumferentially within the shaft and adapted to be coupled to a source of RF energy, the plurality of needle electrodes being selectively deployable from within the shaft to penetrate tissue surrounding the urethra,
        wherein the plurality of needle electrodes are disposed a predetermined distance proximally of the balloon, so that when the balloon is inflated within the bladder and retracted proximally, the balloon engages the bladder neck outlet and disposes the plurality of electrodes at the treatment site.

9. Apparatus as in claim 8 wherein the balloon has a predetermined size.

10. Apparatus as in claim 8 wherein a distal extremity of the balloon is secured to the distal end of the shaft by an atraumatic tip.

11. Apparatus as in claim 8 wherein the balloon when inflated has a substantially spherical configuration.

12. Apparatus as in claim 8 wherein the plurality of needle electrodes are formed of a nickel-titanium alloy.

13. Apparatus as in claim 8 further including means for measuring impedance at the treatment site.

14. Apparatus as in claim 8 further including an introducer and a sheath.

15. Apparatus as in claim 8 further comprising means connected to the handle for supplying a cooling fluid to the elongated shaft so that the cooling fluid is discharged in the vicinity of the needle electrodes.

16. Apparatus as in claim 15 wherein the plurality of needle electrodes are curved.

17. Apparatus as in claim 15 wherein the balloon includes holes through which the cooling fluid is discharged into the vicinity of the needle electrodes.

18. Apparatus as in claim 8 further including means for sensing the temperature of each of one of the plurality of needle electrodes.

19. Apparatus as in claim 18 further including temperature sensing means adapted to sense a temperature of a tissue surface at the treatment site.

20. A method for treatment of female urinary incontinence in a human female having a urinary tract including a urethra and a bladder having a bladder neck outlet the method comprising:
    providing a device having a shaft with proximal and distal ends, a handle secured to the proximal end, an expandable member disposed adjacent the distal end, and a plurality of needle electrodes disposed a predetermined distance proximally of the expandable member and movable between retracted positions within the shaft and extended positions extending from the shaft;

inserting the distal end and expandable member of the device through the urethra, through the bladder neck outlet and into the bladder;

expanding the expandable member within the bladder;

retracting the handle proximally to seat the expandable member against the bladder neck outlet, thereby aligning the plurality of electrodes with the treatment site;

moving the plurality of needle electrodes from the retracted positions to the extended positions to advance the needle electrodes into tissue surrounding the urethra at the treatment site; and supplying radio frequency energy to the plurality of needle electrodes for a predetermined time to remodel tissue surrounding the urethra at the treatment site.

21. A method as in claim 20 further comprising:

moving the plurality of electrodes to the retracted positions;

advancing the device proximally into the bladder to clear the bladder neck outlet and rotating the device through a predetermined angle;

withdrawing the device to reseat the expandable member against the bladder neck outlet;

advancing the plurality of needle electrodes from the retracted positions to the extended positions; and supplying radio frequency energy to the needle electrodes for a predetermined period of time to further remodel tissue surrounding the urethra at the treatment site.

22. A method as in claim 20 further comprising providing a flow of cooling liquid in the urinary tract to cool the urethra in the treatment site.

23. A method as in claim 20 further comprising sensing the impedance of tissue in the vicinity of each one of the plurality of needle electrodes.

24. A method as in claim 20 further comprising:

sensing the temperature of each of the plurality of needle electrodes to ascertain whether a predetermined temperature is being exceeded; and terminating the supply of radio frequency energy to each one of the plurality of needle electrodes when the predetermined temperature for that needle electrode is exceeded.

25. A method as in claim 24 further comprising:

sensing the temperature of tissue in the vicinity of each one of the plurality of needle electrodes; and terminating the supply of radio frequency energy to each one of the plurality of needle electrodes when the temperature of the tissue in the vicinity of that electrode exceeds a predetermined temperature.

* * * * *

UNITED STATES PATENT AND TRADEMARK OFFICE
CERTIFICATE OF CORRECTION

PATENT NO. : 6,470,219 B1
DATED : October 22, 2002
INVENTOR(S) : Stuart D. Edwards, Peter Edelstein and Hong Li It is certified that error appears in the above-identified patent and that said Letters Patent is hereby corrected as shown below:

Column 1,
Line 4, insert -- This application is a continuation-in-part of U.S. patent application Serial No. 09/007,238, filed January 14, 1998 and a continuation-in-part of U.S. patent application Serial No. 09/007,283, filed January 14, 1998. --.

Signed and Sealed this

Sixth Day of June, 2006

JON W. DUDAS
*Director of the United States Patent and Trademark Office*